(12) United States Patent
Bannister

(10) Patent No.: US 6,988,284 B2
(45) Date of Patent: Jan. 24, 2006

(54) SURGICAL TABLES

(75) Inventor: Grahame David Bannister, Lindfield (GB)

(73) Assignee: Eschmann Holdings Limited, West Sussex (GB)

( * ) Notice: Subject to any disclaimer, the term of this patent is extended or adjusted under 35 U.S.C. 154(b) by 178 days.

(21) Appl. No.: 10/250,767

(22) PCT Filed: Jan. 11, 2002

(86) PCT No.: PCT/GB02/00116

§ 371 (c)(1),
(2), (4) Date: Dec. 3, 2003

(87) PCT Pub. No.: WO02/055003

PCT Pub. Date: Jul. 18, 2002

(65) Prior Publication Data

US 2004/0074002 A1 Apr. 22, 2004

(51) Int. Cl.
*A61B 6/00* (2006.01)
*A61G 13/00* (2006.01)

(52) U.S. Cl. .............................. 5/601; 5/600; 378/209

(58) Field of Classification Search ............... 5/601, 5/600, 613, 618, 658, 663; 378/209, 208
See application file for complete search history.

(56) References Cited

U.S. PATENT DOCUMENTS

| | | | | |
|---|---|---|---|---|
| 4,287,422 A | | 9/1981 | Kuphal et al. | 378/209 |
| 4,910,819 A | * | 3/1990 | Brown | 5/484 |
| 4,991,242 A | * | 2/1991 | Brown | 5/601 |
| 5,046,708 A | * | 9/1991 | Schaefer | 5/600 |
| 5,070,520 A | * | 12/1991 | Brown | 378/196 |
| 5,084,927 A | * | 2/1992 | Parkevich | 5/484 |
| 5,133,097 A | | 7/1992 | Pyles | 5/623 |
| 5,396,672 A | * | 3/1995 | Brown | 5/600 |
| 5,422,928 A | * | 6/1995 | Payne | 378/177 |

* cited by examiner

*Primary Examiner*—Robert G. Santos
(74) *Attorney, Agent, or Firm*—Louis Woo

(57) ABSTRACT

A surgical table having a patient support top, at least one section of the top having a metal support supporting an x-ray transparent plate and a moulded cover member fitted to the section to extend across the top and down the sides of the section so as to conceal joins between the support and the plate.

14 Claims, 1 Drawing Sheet

SURGICAL TABLES

Surgical tables have a table top mounted at the upper end of a column the height of which can be adjusted. The table usually has some mechanism for adjusting the angle of the top, which is commonly divided into several separate sections the angle of which relative to one another can be varied. The table top has to be structurally strong in order to support the heaviest of patients and so that it is stable during surgical procedures, which might involve the exertion of high forces. The top, however, should also be transparent to x-rays so that x-ray examination can be performed on the patient in situ. For these reasons, the table top usually has a metal support and a plate of a plastics or other x-ray transparent material secured to the support. X-ray observation of the patient can be made where the patient is supported on the plate. One problem with such table tops is that the join between the plate and the support provides a site for the accumulation of contamination and can be difficult to clean.

It is an object of the present invention to provide an alternative surgical table.

According to one aspect of the present invention there is provided a surgical table having a patient support top, at least one section of the top having a metal support supporting an x-ray transparent plate and a moulded cover member fitted to the section to extend across the top and down the sides of the section so as to conceal joins between the support and the plate.

The cover member is preferably of a plastics material, such as an acrylic, and may be vacuum formed.

According to another aspect of the present invention there is provided a cover member for a table according to the above one aspect of the invention.

A surgical table and its cover member according to the present invention, will now be described, by way of example, Keith reference to the accompanying drawing, in which.

Figure 1:
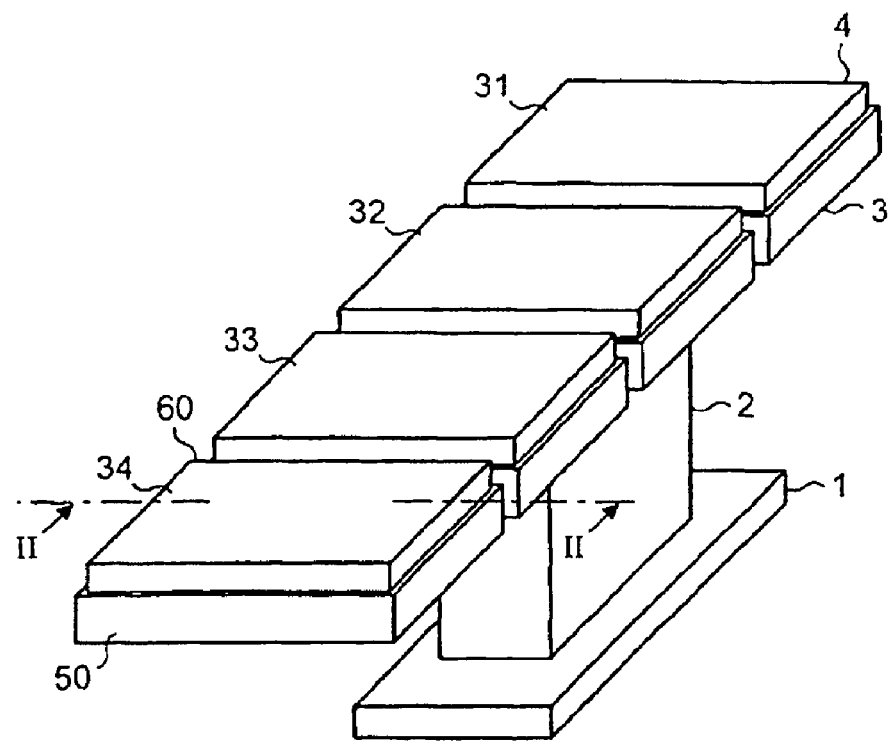
FIG. 1 is a perspective view of the table.

With reference first to FIG. 1, the table includes a base 1, which stands on the floor, a column 2 of adjustable height mounted on the base and a table top 3 providing a patient support surface 4.

The table top 3 is divided into four sections, namely a head section 31, an upper torso section 32, a lower torso section 33 and a leg section 34. The sections 31 to 34 are supported on conventional pivot joints (not shown) and the angles of the sections relative to the column 2 and relative to one another are adjusted by means of conventional actuators (not shown).

Figure 2:
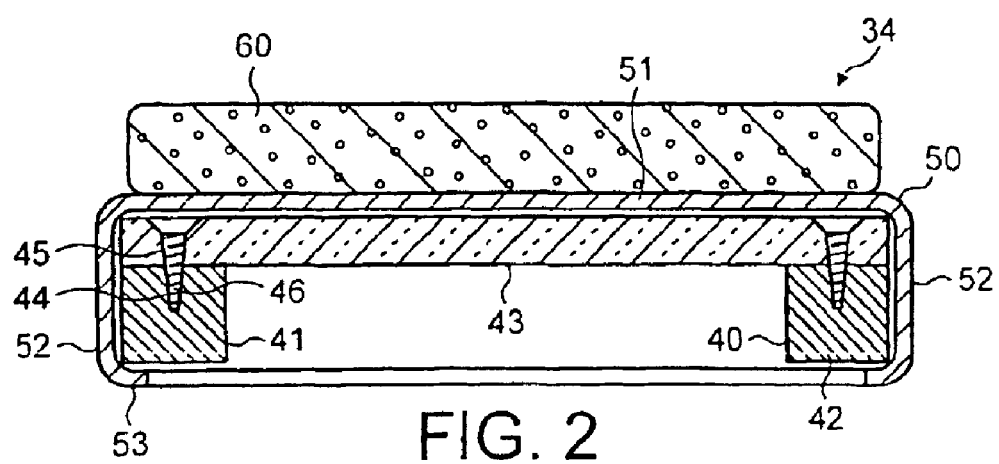
FIG. 2 is a transverse sectional view along the line II—II of FIG. 1.

The construction of each section is the same so only that of one section, the leg section 34, will be described, with reference to FIG. 2. The section 34 has a support 40 of metal, such as steel, including two, rigid side struts 41 and 42 of square section extending parallel to one another. A rigid plate 43 of an x-ray transparent plastics material is supported on the support 40 resting on the upper surface of the struts 41 and 42 and secured to the struts by means of screws 44 extending through holes 45 in the plate and into tapped holes 46 in the struts. It can be seen that the join between the struts 41 and 42 and the plate 43 and the screw holes 45 and 46 all provide potential sites for the accumulation of contamination and present difficulties in cleaning.

The section also includes a cover member 50 vacuum formed from a relatively thin plastics such as an acrylic. The cover 50 is of rectangular shape having a flat central plate 51 and a downwardly-extending peripheral wall 52 extending on all four sides. The lower end of the wall 52 has a narrow, inwardly-projecting lip 53. The shape and size of the cover 50 is such that its plate 51 extends over the tipper surface of the section 34 with the wall 52 extending down the outside of the struts 41 and 42 and with the, lip 53 engaging beneath the struts. The cover 50, therefore, conceals the screw holes 45 and 46 and the join between the support 40 and the plate 43. The cover 50 does not provide any structural support and is relatively thin, enabling the wall 52 to be deformed outwardly over the struts 41 and 42 during fitting, with the lip 53 helping to retain the cover in position. The cover 50 is an integral moulding so that any contamination on its upper and side surfaces can be easily wiped away.

The section is completed by a conventional mattress 60 resting on top of the cover 50.

All four sections 31 to 34 preferably have similar covers 50 shaped to fit the particular section, although, in some cases, it might only be necessary to have covers on those sections most likely to be exposed to contamination. The cover can be provided at low cost so that it can be replaced when damaged without the need to replace other parts of the table.

What is claimed is:

1. A surgical table having a patient support top, at least one section of the top having a metal support supporting an x-ray transparent plate and a moulded cover member fitted to the section to extend across the top and down the sides of the section so as to conceal joins between the support and the plate.

2. A surgical table according to claim 1 wherein the cover member is of a plastics material.

3. A surgical table according to claim 2 wherein the plastics material is an acrylic material.

4. A surgical table according to any foregoing claim wherein the cover member is vacuum formed.

5. A surgical table according to any foregoing claim wherein the cover member is an integral moulding and has a flat central plate and a downwardly-extending peripheral wall extending on all sides thereof.

6. A surgical table according to claim 5 wherein a lower end of the wall has an inwardly-projecting lip.

7. A surgical table according to claim 6 wherein the shape and size of the cover member are such that the plate extends over the upper surface of the section with the wall extending down the outside of the section with the lip engaging beneath the section.

8. A surgical table according to any one of claims 5 to 7 wherein the wall is adapted to be deformable outwardly over the section during fitting, with the lip retaining the cover member in position.

9. A surgical table according to any foregoing claim wherein the metal support includes two rigid side struts extending parallel to one another and the x-ray transparent plate is rigid and is supported on the support by resting on upper surface of the struts.

10. A surgical table according to claim 9 wherein the x-ray transmitting plate is secured to the struts by means of screws extending through holes in the x-ray transparent plate and into tapped holes in the struts.

11. A surgical table according to any foregoing claim further comprising a mattress resting on top of the cover member.

12. A surgical table according to any foregoing claim wherein the patient support top is divided into four sections comprising a head section, an upper torso section, a lower torso section and a leg section, and each section is provided with a respective cover member shaped to fit the respective section.

13. A moulded cover member for fitting to a section of a patient support top of a surgical table, wherein the cover member is of an integrally moulded plastics material and has a flat central plate, a downwardly-extending peripheral wall extending on all sides thereof and an inwardly-projecting lip at a lower end of the peripheral wall.

14. A moulded cover member according to claim 13 wherein the peripheral wall is adapted to be deformable outwardly during fitting of the cover member to the section.

* * * * *